United States Patent
Brumboiu et al.

(10) Patent No.: US 6,974,705 B1
(45) Date of Patent: Dec. 13, 2005

(54) METHOD FOR DETERMINING THE CONCENTRATION OF GAS IN A LIQUID

(75) Inventors: Aurel D. Brumboiu, Calgary (CA); Darrell A. Norquay, Calgary (CA)

(73) Assignee: Datalog Technology Inc., Calgary (CA)

( * ) Notice: Subject to any disclaimer, the term of this patent is extended or adjusted under 35 U.S.C. 154(b) by 0 days.

(21) Appl. No.: 09/519,741

(22) Filed: Mar. 6, 2000

(51) Int. Cl.$^7$ ................................................. G01N 1/22
(52) U.S. Cl. .................. 436/181; 73/19.01; 73/19.1
(58) Field of Search ................... 436/181; 73/19.01, 73/19.1

(56) References Cited

U.S. PATENT DOCUMENTS

| | | | | |
|---|---|---|---|---|
| 4,731,732 A | * | 3/1988 | Warchol et al. | 700/147 |
| 5,317,932 A | * | 6/1994 | Westlake et al. | 73/863.23 |
| 5,469,917 A | * | 11/1995 | Wolcott | 166/250.01 |
| 5,528,923 A | * | 6/1996 | Ledez et al. | 73/19.02 |
| 5,729,342 A | * | 3/1998 | Yokoyama et al. | 356/319 |
| 6,192,737 B1 | * | 2/2001 | Ohlrogge et al. | 261/104 |

FOREIGN PATENT DOCUMENTS

WO          98/57131      * 12/1998

* cited by examiner

*Primary Examiner*—Jill Warden
*Assistant Examiner*—L. Cross
(74) *Attorney, Agent, or Firm*—Bennett Jones LLP

(57) ABSTRACT

A method for determining a correction factor for use in analysing the concentration of a gas in a liquid is described. The correction factor is determined by measuring the output concentration of the gas in the liquid as the gases saturation limit in that liquid. The method is useful with gas permeable membrane technology to measure the concentration of the gas in the liquid. The method includes applying a correction factor to give the true concentration of gas in the liquid taking into account both that gas in solution in the liquid and that amount of gas present as entrained bubbles in the liquid.

59 Claims, 2 Drawing Sheets

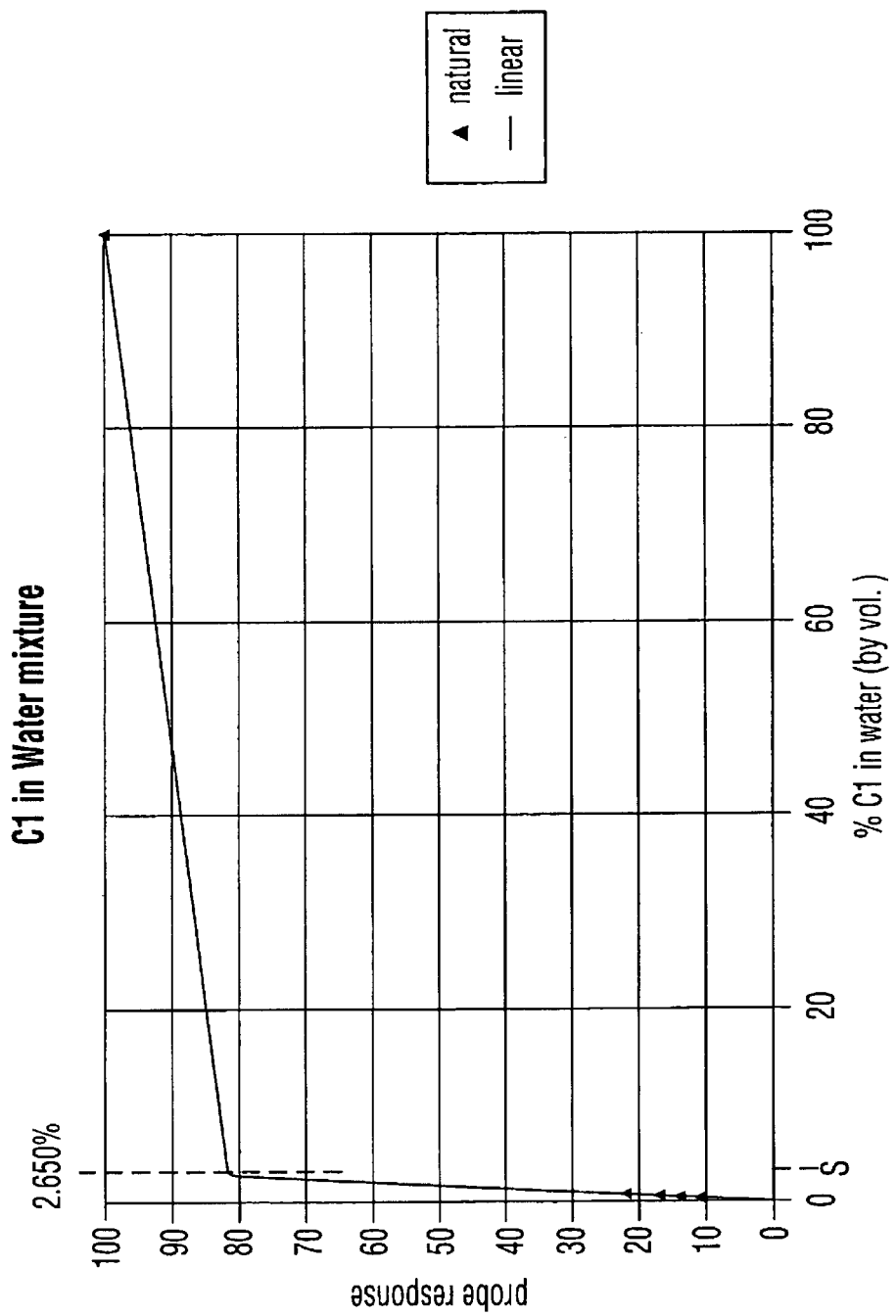

METHOD FOR DETERMINING THE CONCENTRATION OF GAS IN A LIQUID

FIELD OF THE INVENTION

The present invention is directed to a method for determining the concentration of a gas in a liquid and, in particular, to a method for determining a correction factor and for using the correction factor in determining the concentration of a gas in a liquid.

BACKGROUND OF THE INVENTION

The process of drilling an oil/gas well liberates gases from the formation, which are carried to the surface by the drilling fluid. The measurement of this liberated gas at the surface is a well-established method of qualitatively indicating the gas/oil content of the formation being drilled. However, because of the limitations of methods of gas-sampling from the fluid, the current and prior methods for measurement preclude the direct quantitative measurement of these gases as a percentage by volume of the drilling fluid.

One current sampling device is known as a "gas trap" or "mechanical agitator". Gas traps are unable to measure quantitatively gases in drilling mud. A gas trap is, in essence, a mechanical converter that converts a percentage of gas in the mud to a percentage of gas in air, which can be directly measured. Dissolved gases are broken out by mechanical agitation, and removed by gas sampling equipment through a sample line to an analysis device. As long as the total gas percentage in the drilling fluid remains within the soluble range, air will be re-introduced into the trap at approximately the same rate as the sample is drawn out. In this case, the percentage of gas measured will be proportional to the actual percentage in solution, depending on the efficiency factor of the trap. As the gas percentage in the mud increases, however, it will reach a point where the mud is saturated with all the gas that can be held in solution, and the remaining gas will exist as free bubbles forming froth in the drilling fluid. These bubbles will displace air in the trap canister. This falsely increases the apparent concentration at the sampling point. Current gas-trap based measuring systems exhibit large non-linearity in response due mainly to this required conversion between gases in solution and gases in the form of froth in the liquid.

The gas trap is not the only problem with the current system of gas measurement. Since the gas analyzer is remote from the trap, a sampling system is required to draw the gas sample from the trap to the analyzer through small diameter tubing. This introduces other variables into the analysis, such as the sample draw rate, temperature effects on the sample as it passes through the tubing, integration of sample peaks by long lengths of tubing, delays caused by the sampling tubing length, etc. These, along with a myriad of other variables in the analysis process, have substantially precluded accurate quantitative analysis of gas in drilling fluids. This has made it difficult or impossible to form quantitative comparisons of data between similar oil/gas wells in the same field, or from the same formation in different fields. The development of a method for accurately determining well bore gas concentration data without the necessity of expensive intrusive measurements such as Drill Stem Testing has been a goal of the industry for many years. Such a method would permit the comparison of surface-gathered data from different wells to determine the relative oil/gas content of a given formation.

Gas permeable membrane probes, such as the GasWizard™ instrument (Datalog Technology Inc.: Calgary, Alberta, Canada) are now available that are capable of determining the concentration of a gas directly in a liquid. Thus, the gas permeable membrane probes address the problems of gas detection using a gas trap and remote analyzer by eliminating the conversion step from gas in mud to gas in air. With the elimination of this conversion, it is possible to directly read the gas concentration in the mud system. It also eliminates many of the problems incurred by remote sampling of the gas stream.

A gas permeable membrane probe consists of a flexible probe with a gas permeable membrane at its end. The gas permeable membrane is immersed in the drilling fluid at or near the point where the fluid exits the well bore. This probe is attached to a measuring instrument in a watertight, explosion proof enclosure, which contains the necessary microprocessor based electronic and pneumatic controls for operating the probe, along with a compact gas analyzer for the measurement of gases absorbed at the probe. The device outputs collected data via a serial communications link which may be attached to a remote computer for data logging and additional analysis.

Gas permeable membrane probes are based on gas permeable membrane technology described in U.S. Pat. No. 5,317,932 by Westlake and Wolcott. The use of the probe to sample oil-drilling muds is described in U.S. Pat. No. 5,469,917 of Wolcott.

While the use of gas permeable membrane probes has improved the measurement of gas concentrations in drilling mud, it is still difficult to measure quantitatively the concentration of gas in drilling mud. In particular, since the probe is calibrated in either air or liquid, the probe cannot correctly measure gas concentration where the drilling mud is saturated with gas and some gas is present both in solution and as froth in the drilling mud.

A method is needed for measuring accurately and quantitatively the concentration of a gas in a liquid, such as drilling mud.

SUMMARY OF THE INVENTION

A method for determining quantitatively the concentration of a gas in a liquid has been invented. The method includes measuring the concentration of the gas in the liquid that may contain bubbles and then applying a correction factor to give the true concentration of gas in the liquid taking into account both that concentration of gas in solution in the liquid and that concentration of gas present as froth in the liquid. This method permits automatic and continuous correction of the measured gas concentration values to output accurate quantitative percent-by-volume measurements of a gas in a liquid. Although this method was developed for use with gas permeable membrane probe devices, it is believed that it can be applied to other methods for measuring the concentration of gas in a liquid and it is believed that it will be useful with other detection or measurement devices that measure gas concentration in a liquid.

Thus, in accordance with a broad aspect of the present invention, there is provided a method for obtaining a correction factor for measuring a concentration of gas in a liquid using a gas in liquid concentration measurement device, the method comprising: obtaining the solubility threshold for the gas in the liquid; ensuring that the device is calibrated for concentrations of about 0% gas in liquid and about 100% gas; using the device to conduct sufficient measurements of the gas concentration at known actual concentrations to permit generation of a first function representing measured concentration versus actual concentration below the solubility threshold; determining a measured concentration at about the solubility threshold; using the measured concentration at about the solubility threshold to determine a second function representative of measured concentration versus actual concentration above the solubility threshold; and using the first function and the second function to generate the correction factor.

In accordance with another broad aspect of the present invention, there is provided a method for obtaining a correction factor for measuring a concentration of gas in a liquid using a gas in liquid concentration measurement device, the method comprising: obtaining the solubility threshold for the gas in the liquid; ensuring that the device is calibrated for concentrations of about 0% gas in liquid and about 100% gas; using the device to conduct sufficient measurements of the gas concentration at known actual concentrations to permit generation of a first function representing measured concentrations versus actual concentration below the solubility threshold; using the measured concentrations and the solubility threshold to fully define the first function and deducing a theoretical response at about the solubility threshold; using the theoretical response at about the solubility threshold to determine a second function representative of measured concentration versus actual concentration for the region above the solubility threshold; and using the first function and the second function to generate the correction factor.

In accordance with other broad aspects of the present invention, there are also provided a method for determining the concentration of a selected gas in a selected liquid; a method for preparing a concentration measurement device for use; and a system for operating a gas in liquid concentration measuring device.

BRIEF DESCRIPTION OF THE DRAWINGS

A further, detailed, description of the invention, briefly described above, will follow by reference to the following drawings illustrating use of the invention. These drawings depict only typical applications of the invention and are therefore not to be considered limiting of its scope. In the drawings:

FIG. 3 is a concentration response curve for methane in water at standard temperature and pressure created according to the present invention.

DETAILED DESCRIPTION OF THE PREFERRED EMBODIMENTS

One method according to the present invention determines a correction factor to be applied when using a device for measuring gas concentration in a liquid. Another method is for measuring the concentration of a gas in a liquid using a gas measurement device and applying a correction factor to give the true concentration of the gas in the liquid taking into account both that amount of gas in solution in the liquid and that amount of gas present as entrained bubbles forming froth in the liquid.

Gases in fluids exist in two distinct phases; in solution and as bubbles. Generally, behavior of a gas in solution in a liquid differs greatly from the behavior of the same gas in bubble form in the liquid. Different types of fluids (including air) exhibit different solubility factors for any particular gas. Most gases might be considered to have 100% "solubility" in air since air is also a gas. A gas permeable membrane probe, or other device for determining the concentration of a gas in a fluid, can easily be calibrated for % gas (either automatically or by manually recording a difference) in air by inserting the device into a known percentage of the gas in the air. This calibrates the instrument to read quantitatively the direct percent gas by volume in air. This is the easiest and most convenient way to calibrate a gas concentration measurement device such as a gas permeable membrane probe and, if measurements of percentage gas in air are desired, no further processing is required.

A gas will exhibit a solubility in a liquid that is different than its solubility in another liquid or in air. Thus, if a device for determining the concentration of a gas in a fluid is calibrated in a known percent by volume gas in air mixture and then inserted in an identical percent by volume gas in liquid mixture, the device will often show a concentration different than the actual concentration. For example, if a gas permeable membrane probe is calibrated in air containing a known concentration of methane by percent volume and the probe is then inserted into an identical (by percent volume) mixture of methane in water, the probe will generally read a much higher percentage of gas than actually exists. While this discrepancy can be addressed by calibration of the device for % gas in liquid below the solubility threshold (also termed the maximum solubility or saturation point), simple calibration is not useful where the liquid contains the gas both in solution and as entrained bubbles.

It has been determined, according to the present invention, that a gas concentration measurement device will have a first response in a liquid having a concentration of gas below the solubility threshold for that combination of gas and liquid and a second response in a liquid having a concentration of gas above the solubility threshold.

Figure 1:
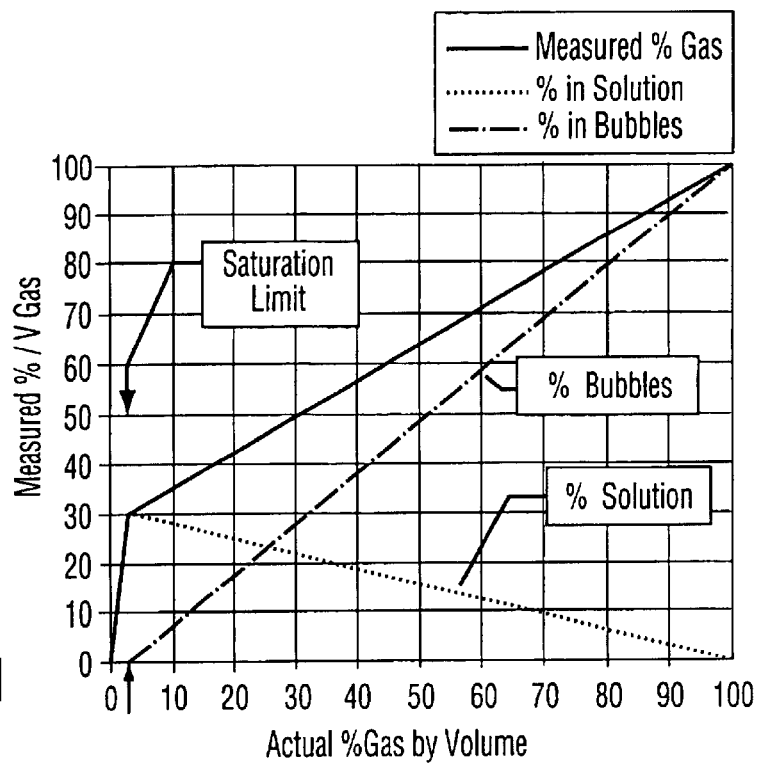
FIG. 1 is a membrane response curve for a gas in a liquid.

Referring to FIG. 1, a response curve for a gas permeable membrane is shown for a gas having a solubility threshold of, for example, 3% in a liquid. The gas permeable membrane was calibrated in air. The curve was prepared according to one aspect of the present invention. By plotting measured % gas concentration against actual % gas concentration (both by volume), you get a curve which shows that, for concentrations less than the maximum solubility of the gas in the liquid, the curve has a very steep slope. Actual concentrations of the gas in the liquid of from 0% to 3% by volume read an equivalent of about 0 to 30% when measured by the gas permeable membrane, so the comparison, when plotted, results in a curve having a slope of about 10.

In liquid samples containing actual concentrations of the gas that are higher than the saturation point of the gas in the liquid, the measured gas concentration rises at just less than a 1:1 ratio, with increases in the actual gas concentration (i.e. if the gas in liquid concentration by volume increases by 1%, the measured gas concentration increases by less than 1%). When plotted, the portion of the response curve above the solubility threshold has a much shallower slope that that portion below the solubility threshold.

Thus, in a plot of the actual versus measured concentration for the gas in the liquid a "dogleg" curve is formed which has 2 distinct slopes. The slope of the curve below the saturation point is about 10 while the slope of the curve above the saturation point has a slope of less than 1. The curve has endpoints at 0% gas in liquid and 100% gas (by volume).

Looking more closely at FIG. 1, the concentration of the gas measured in the liquid consists of two distinct phases around the saturation limit. The portion of the measured curve representing the gas in solution increases rapidly as the overall concentration is increased up to the solubility threshold in the liquid in this example of about 3% by volume. After this point, the gas in solution then begins to decline slowly toward zero as the percent of gas froth increases and begins to displace a volume of liquid. In theory, the gas cannot begin to exist as froth bubbles until the saturation point has been exceeded. However, in practice this is not a sharply defined inflection point. There will always be a region in which there exist both bubbles and dissolved gas around the saturation point of the curve. Ideally, the % gas as froth in the liquid rises from zero beginning at the saturation point. As the total concentration is increased beyond the saturation point, increasingly more of the total amount of gas is in bubble form, displacing some of the liquid, until a concentration of 100% gas is reached, at which point no more liquid is present. This assumes a constant volume. As more gas is introduced, an equal amount of liquid is necessarily displaced and thus, the amount of gas in solution decreases to zero. The overall representation of the gas by percent volume in the liquid above the saturation point is the sum of the bubble curve and the solution curve.

The characteristic curves for all gases in fluids (and air as well) will have two common end points, i.e. 0% gas concentration, and 100% gas concentration. At 0% concentration, obviously there is no gas to measure and the measurement can be adjusted to zero regardless of the fluid type. At 100% gas concentration, there is only gas present (assuming a constant volume) and again the measured concentration is unaffected by gas or fluid type. Between these two points, a mathematical model as described above exists. Below the saturation point of the gas in the liquid, the measured concentration is determined by only the amount of gas in solution, while above the saturation point it is determined by the maximum soluble gas plus the free gas present as entrained bubbles.

Thus, in view of the foregoing and in accordance with the present invention, a correction factor can be determined for use with a device for determining gas in liquid concentrations such that the device is useful for quantitatively determining the concentration of a selected gas in a selected liquid. The correction factor is applied to the measured gas concentration to obtain an output gas concentration which corresponds to the actual gas concentration. Of course the ideal output gas concentration is equal to the actual gas concentration.

The correction factor is determined for a gas in liquid concentration measurement device. To determine the correction factor, the solubility threshold for the gas and liquid combination must be obtained. This can be obtained by use of texts such as Lange's Handbook of Chemistry 14$^{th}$ ed., John H. Dean MacGraw-Hill, Inc. 1992, Section 5, Table 5.1. Alternatively a static test, as is known, can be conducted. The device must also be calibrated to generate a measured concentration of 0% gas when analysing a sample of about 0% gas and to generate a measured concentration of 100% gas when analysing a sample of about 100% gas. When using the method with a gas permeable membrane device, it is preferred that any calibration be conducted using a probe wetted with the liquid of interest to avoid boundary layer errors.

The device is then used to make sufficient measurements of the gas concentration at known actual concentrations to permit the generation of a first function representing the measured concentration versus the actual concentration below the solubility threshold. To do this, one or more solutions having selected concentrations of gas are prepared according to know procedures and the gas concentration of these solutions are measured using the device for measuring gas concentration in a liquid. The measured concentration versus the actual concentration is recorded for each of the solutions. As will be appreciated sufficient measurements can be only one, since with the known value of 0%, there will be enough values to generate a function. However, in a preferred embodiment more than one measurement is made at known concentrations in order to determine the first function with greater certainty. Since it is much easier to work with mixtures containing the gas completely in solution in the liquid (i.e. gas concentrations well below the solubility threshold) and since most devices will measure such concentrations more accurately, preferably, the first function is generated using mixtures having gas concentrations of less than about half of the gas concentration at the solubility limit and most preferably using mixtures having gas concentrations of less than about one third of the gas concentration at the solubility limit.

The measured concentration at the solubility threshold can then be used to determine a second function representative of the measured concentration versus the actual concentration in the region above the solubility threshold. The second function is determined by using the measured concentration at about the solubility threshold and the known measured concentrations of 100%.

The measured concentration at the solubility threshold can be either directly measured or determined based on the first function. Direct measurement of the solubility threshold should be used only where the system provides for accurate measurements of concentrations around the solubility threshold can be made. The concentrations of liquid/gas mixtures around the solubility threshold are often very difficult to measure. Therefore, it is generally preferred to determine the measured concentration at the solubility threshold by deducing a theoretical response based on the first function.

The rate of change of measured concentrations versus actual concentrations for many devices is assumed to be linear. Thus, preferably the first function and the second function are each linearized to facilitate generation and application thereof.

The first and second functions are used to generate the correction factor. Once the correction factor is determined, it can be applied in various ways to correct the output of the gas measurement device. As an example, the correction factor can be the difference between the values generated by the first function or the second function and the actual gas concentration at any particular concentration of gas in liquid between 0% and 100%. The difference can be applied to the measured concentration to obtain an output gas concentration. The difference values can be stored for any particular combination of liquid and gas and applied continuously to measured concentrations in order to obtain corrected output concentrations.

In a preferred embodiment, the correction factor is generated as the inverse functions of the first and second functions. The inverse function can be applied continuously to the measured gas concentration to obtain an output gas concentration.

Figure 2:
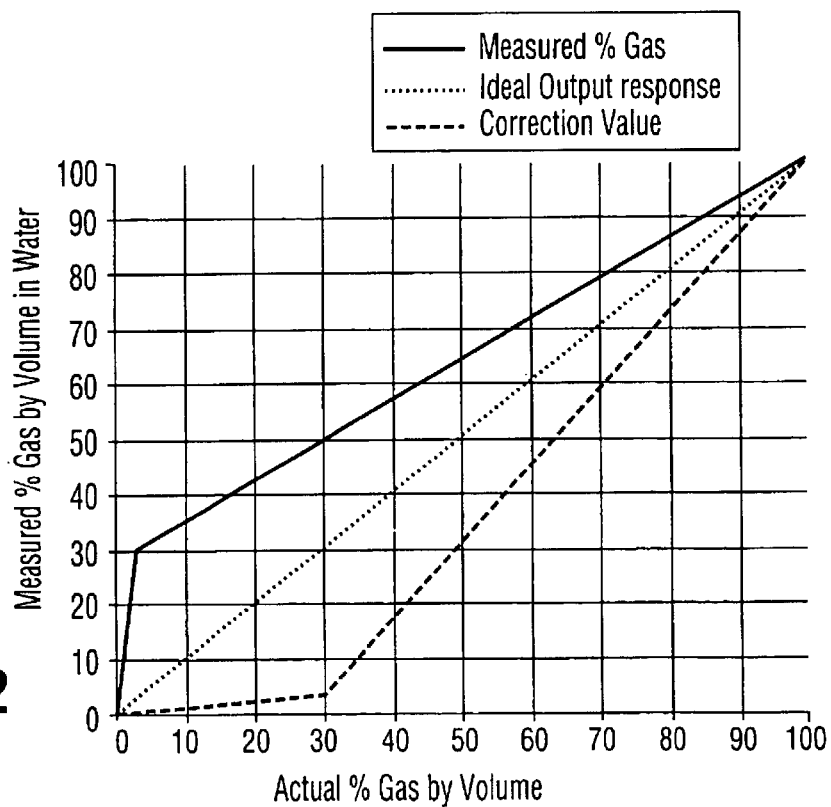
FIG. 2 is a concentration response curve for a gas in a liquid.

A concentration response curve for a gas in water is shown in FIG. 2. The solubility threshold of the gas in the water is 3%. The measured concentration response curve is comprised of a first portion 10 representative of a first function and a second portion 12 representative of a second function. This figure shows one model for applying the correction factor wherein the correction factor is the inverse function of the measured concentration response curve. The correction factor is applied to the measured concentration to obtain the linear output concentration curve which is corrected for the concentration in the liquid. Thus we get a straight line from 0%–100% representing the output gas concentration in percent by volume in the liquid, which is mathematically derived from the measured values.

According to the present invention, concentration response curves and/or correction factors can be obtained for any combination of gas and liquid and at a plurality of conditions, such as various temperature and/or pressure conditions. The concentration response curves and/or correction factors can be applied in systems such as, for example, software for controlling a device for determining gas in liquid concentrations. Preferably any system for using correction factors includes correction factors for a plurality of gas/liquid mixtures and permits the user to select the liquid and gas mixture and temperature/pressure conditions in which the gas concentration determining device is operating.

The system for controlling the operation of a device requires a function for obtaining a concentration measurement such as, for example, by input or by connection to a gas in liquid concentration measurement device. The device also requires a function for storing and applying the correction factor to any concentration measurements obtained. It will be appreciated that such functions can be provided in software using for example a programmable logic controller or a personal computer.

Once a correction factor is obtained for a particular device, it can be applied to the operation of other similar devices without modification. It will be appreciated that similar devices are those operating on the same basic technology. Where an operating system using a correction factor according to the present invention is desired to be used in another device, simple error tests using solutions of known concentration can be conducted to determine whether the devices are similar enough to properly support the transfer.

The methods of the present invention can be used for monitoring drilling fluids during the drilling of an oil/gas well. Different drilling fluid bases such as, for example, diesel, water or polymer, can be accommodated by applying the method. In drilling fluid monitoring, often the gas of interest is methane. The presence of methane in the drilling fluid is indicative of the presence of hydrocarbon bearing formations. Water and water based muds show similar but not identical solubility for methane, wherein the saturation limit is in the range of about 3% at STP. Oil based muds show a much higher solubility limit for methane, for instance diesel invert mud is around 9% by volume, and mineral oil based mud is around 15%. Thus their response curves, when plotted, have different slopes and different breakpoints, but the same ultimate endpoints at 0% and 100% by volume concentrations.

EXAMPLE

A correction factor for the determination of methane concentration in water for use with a gas permeable membrane device was sought. The tests were conducted at: 31 to 34° C. and standard atmospheric pressure. From texts it was determined that the average solubility threshold for methane in water at these conditions was 2.650% by volume. GasWizard™ gas detection equipment was used to obtain gas concentration measurements. The equipment was already calibrated for 0% concentration. The equipment was calibrated to read 100% at an actual 100% gas concentration using pure methane gas. The calibration was carried out using a gas permeable membrane probe that had been wetted in water. This provided a boundary layer on the probe that was specific for use in water.

The response curve for methane in water was generated first by using mixtures of methane in water having known concentrations of methane in the methane soluble region (ie. below the solubility threshold). These measurements were used to extrapolate the device's measurement at the solubility threshold. The measurement at the solubility threshold was then used with the measurement response of the device at 100% to obtain the response curve in the region above the solubility threshold.

For a gas concentration measurement device, the response curve (measured versus actual concentration values) regions above and below the solubility threshold are generally linear. On a graph of the response curve, the function for the first of these regions is $y=m_1 x$ where x is the gas concentration (by volume). When x is less than the solubility threshold (S), the slope $m_1$ can be determined experimentally by injecting different gas amounts into a known amount of liquid. The results are improved if the gas amounts injected result in solutions well below the solubility point. This ensures that no bubbles are formed and that the whole amount of the injected gas is dissolved. After finding the slope $m_1$ for the zone below the solubility threshold, the function is applied to extend the line through the solubility threshold such that x=S and the response $y_s$ at the solubility threshold can be calculated. In particular, using $y_s=m_1 S$.

Then according to the method a linear curve is generated between the solubility threshold and the 100% gas concentration ($y_{100}$) that was previously calibrated. The upper region of the response curve is represented by the function $y=m_2 x+b$.

The upper region slope being $m_2=y_{100}-y_s$ 100−S

And the y intercept being $b=y_{100}-100 m_2$.

In the example, solutions were prepared having methane in water concentrations of:

0.268%C1 by volume
0.335%C1 by volume
0.470%C1 by volume and
0.738%C1 by volume.

These solutions were measured using the gas permeable membrane device and the following measured concentrations were obtained.

| Actual concentration (% vol) | Measured concentration (% vol) |
|---|---|
| 0 | 0 |
| 0.268 | 10.86 |
| 0.335 | 13.95 |
| 0.470 | 16.97 |
| 0.738 | 22.3 |
| 100 | 100 |

With reference to the above-noted discussion, the functions were obtained as graphically depicted in FIG. 3. The inverse function of the resulting curve was used to correct methane in water measured concentrations determined using a gas membrane device.

The inverse function was used in software to correct concentrations measured using a gas membrane device.

To verify that the second function behavior was as predicted, (i.e. the function above the solubility threshold was correct) mixtures were prepared and measurements made as follows:

| Actual concentration (% vol) | Measured concentration (% vol) |
|---|---|
| 14.63 | 82.0 |
| 18.12 | 84.6 |
| 20.8 | 85.0 |
| 24.49 | 86.8 |

These measurements agreed very closely with formula 2 of FIG. 3.

Data was also collected to obtain device measurements closer to the solubility threshold. The experimental system that was used to create liquid/gas flowing mixtures for measurement using a gas permeable membrane probe created significant turbulence in the liquid resulting in the generation of bubbles below the actual saturation limit. This turbulence resulted in a deviation from the linear behavior around the solubility threshold and difficulty reproducing results.

Experimental mixtures containing gas concentrations above about 25% by volume were impossible to produce with existing equipment.

It will be apparent that many other changes may be made to the illustrative embodiments, while falling within the scope of the invention and it is intended that all such changes be covered by the claims appended hereto.

The embodiments of the invention in which an exclusive property privilege is claimed are defined as follows:

1. A method for determining a mathematical function representative of measured concentration versus actual concentration of a gas in a liquid when the gas is at a concentration in the liquid above a solubility threshold for the gas in the liquid, the method comprising:

obtaining the solubility threshold for the gas in the liquid;

ensuring that the device is calibrated for concentrations of about 0% of the gas in the liquid and about 100% of the gas;

using the device to conduct sufficient measurements of the gas concentration at known actual concentrations to permit generation of a first mathematical function representing device-measured concentrations versus actual concentrations of the gas in the liquid below the solubility threshold of the gas in the liquid;

applying the first mathematical function to deduce a theoretical device-response at about the solubility threshold; and using the theoretical device-response at about the solubility threshold and the device calibrated response at 100% gas concentration to determine the mathematical function representative of the response of the gas-in-liquid concentration measurement device when the concentration of gas is above the solubility threshold, the mathematical function defining the device-measured concentration versus actual concentration for the region above the solubility threshold wherein the actual concentration for the region above the solubility threshold includes a solubilized amount of gas that is solubilized in the liquid and the gas that is present in bubble state.

2. The method of claim 1 wherein sufficient measurements is one measurement between 0% concentration of the gas in the liquid and the concentration of the gas in the liquid at the solubility threshold.

3. The method of claim 1 wherein sufficient measurements is at least two measurements.

4. The method of claim 1 wherein the known actual gas concentrations are less than about half of the gas concentration at the solubility threshold.

5. The method of claim 1 wherein the first mathematical function and the mathematical function representative of the response of the gas-in-liquid concentration measurement device are each linear.

6. The method of claim 1 further comprising generating a correction factor for use with the measurement device, the correction factor being the difference between a value of the first mathematical function or the mathematical function representative of the response of the gas-in-liquid concentration measurement device and an actual gas concentration corresponding to that value and the difference is recorded and applied to any device-measured concentrations corresponding to the value.

7. The method of claim 1 further comprising generating a correction factor for use with the measurement device, the correction factor being generated as the inverse functions of the first mathematical function and the mathematical function representative of the response of the gas-in-liquid concentration measurement device.

8. The method according to claim 1 wherein the device is a gas semipermeable membrane device.

9. The method of claim 1 wherein the step of obtaining the solubility threshold is performed at any time prior to the step of applying the first mathematical function.

10. A method for determining a mathematical function representative of measured concentration versus actual concentration of a gas in a liquid when the gas is at a concentration in the liquid above a solubility threshold for the gas in the liquid, the method comprising;

obtaining the solubility threshold for the gas in the liquid;

ensuring that the device is calibrated for concentrations of about 0% of the gas in the liquid and about 100% of the gas;

using the device to conduct sufficient measurements of the gas concentration at known actual concentrations to permit generation of a first mathematical function representing device-measured concentration versus actual concentration of the gas in the liquid below the solubility threshold of the gas in the liquid;

determining a measured concentration at about the solubility threshold; and using the measured concentration at about the solubility threshold and the device calibrated response at 100% gas concentration to determine the mathematical function representative of the device-measured concentration versus actual concentration above the solubility threshold when the gas is in a bubble state in the liquid.

11. The method of claim 10 wherein the measured concentration at about the solubility threshold is measured using the device.

12. The method of claim 10 wherein the measured concentration at about the solubility threshold is determined by extrapolation of the first mathematical function.

13. The method of claim 10 wherein sufficient measurements is one measurement between 0% concentration of the gas in the liquid and the concentration of the gas in the liquid at the solubility threshold.

14. The method of claim 10 wherein sufficient measurements is at least two measurements.

15. The method of claim 10 wherein the known actual gas concentrations are less than about half of the gas concentration at the solubility threshold.

16. The method of claim 10 wherein the first mathematical function and the second mathematical function are each linear.

17. The method of claim 10 wherein the device is a gas semipermeable membrane device.

18. The method of claim 10 wherein the step of obtaining the solubility threshold is performed at any time prior to a step wherein the solubility threshold must be known.

19. A method for using a concentration determining device to measure the concentration of a selected gas in a selected liquid, comprising:
   obtaining a correction factor for measuring the concentration of the selected gas in the selected liquid using the device by obtaining the solubility threshold for the selected gas in the selected liquid; ensuring that the device is calibrated for concentrations of about 0% selected gas in selected liquid and about 100% selected gas; using the device to conduct sufficient measurements of the gas concentration at known actual concentrations of the selected gas in the selected liquid to permit generation of a first mathematical function representing device-measured concentration versus actual concentration of the selected gas in the selected liquid below the solubility threshold; determining a measured concentration at about the solubility threshold; using the measured concentration at about the solubility threshold and the device calibrated response at 100% gas concentration to determine a second mathematical function representative of device-measured concentration versus actual concentration above the solubility threshold, wherein the actual concentration of the selected gas in the selected liquid includes an amount of solubilized gas and an amount of the gas in bubble state; and using the first mathematical function and the second mathematical function to generate the correction factor, the correction factor being one of (i) the difference between a value of the first mathematical function or the second mathematical function and an actual gas concentration corresponding to that value or (ii) the inverse functions of the first mathematical function and the second mathematical function; and
   recording the correction factor for application to any device-measured results by the device.

20. The method as defined in claim 19 wherein the correction factor is plotted for the selected gas in the selected liquid.

21. The method as defined in claim 19 wherein the correction factor is included in a system for operating the device.

22. The method of claim 19 wherein sufficient measurements is one measurement between 0% concentration of the selected gas in the selected liquid and the concentration of the selected gas in the selected liquid at the solubility threshold.

23. The method of claim 19 wherein sufficient measurements is at least two measurements.

24. The method of claims 19 wherein the known actual concentrations are less than about half of the gas concentration at the solubility threshold.

25. The method of claim 19 wherein the first mathematical function and the second mathematical function are each linear.

26. The method of claim 19 wherein the measured concentration at about the solubility threshold is determined by extrapolation of the first mathematical function.

27. The method of claim 19 wherein the measured concentration at about the solubility threshold is obtained using the device.

28. The method according to claim 19 wherein the concentration determining device is a gas membrane device.

29. The method of claim 19 wherein the step of obtaining the solubility threshold is performed at any time prior to a step wherein the solubility threshold must be known.

30. A method for determining a concentration of a selected gas in a selected liquid, the method comprising:
   providing a device for determining gas-in-liquid concentrations;
   using the device to obtain a concentration measurement of the selected gas in the selected liquid; and
   applying a correction factor to the concentration measurement to produce an output concentration measurement of the selected gas in the selected liquid, the correction factor being obtained by using a device similar to the device for determining gas-in-liquid concentrations and obtaining the solubility threshold for the selected gas in the selected liquid; ensuring that the similar device is calibrated for concentrations of about 0% selected gas in selected liquid and about 100% selected gas; using the similar device to conduct sufficient measurements of the selected gas concentration at known actual concentrations to permit generation of a first mathematical function representing measured concentration versus actual concentration below the solubility threshold of the selected gas in the selected liquid; determining a measured concentration at about the solubility threshold; using the measured concentration at about the solubility threshold and the device calibrated response at about 100% selected gas concentration to determine a second mathematical function representative of measured concentration versus actual concentration above the solubility threshold, wherein the actual concentration of the selected gas in the selected liquid includes an amount of solubilized gas and an amount of the gas in bubble state; and using the first mathematical function and the second mathematical function to generate the correction factor, the correction factor being one of (i) the difference between a value of the first mathematical function or the second mathematical function and an actual gas concentration corresponding to that value or (ii) the inverse functions of the first mathematical function and the second mathematical function.

31. A method according to claim 30 wherein the device is a gas membrane device.

32. The method of claim 30 wherein sufficient measurements is one measurement between 0% concentration of the selected gas in the selected liquid and the concentration of the selected gas in the selected liquid at the solubility threshold.

33. The method of claim 30 wherein sufficient measurements is at least two measurements.

34. The method of claim 30 wherein the known actual concentrations are less than about half of the gas concentration at the solubility threshold.

35. The method of claim 30 wherein the first mathematical function and the second mathematical function are each linear.

36. The method of claim 30 wherein the measured concentration at about the solubility threshold is determined by extrapolation of the first mathematical function.

37. The method of claim 30 wherein the measured concentration at about the solubility threshold is obtained using the similar device.

38. The method of claim 30 wherein the similar device is the device provided and used to obtain the concentration measurement.

39. The method of claim 30 wherein the step of obtaining the solubility threshold is performed at any time prior to a step wherein the solubility threshold must be known.

40. A method for obtaining a correction factor for measuring a concentration of a gas in a liquid using a gas-in-liquid concentration measurement device, the method comprising:
   obtaining the solubility threshold for the gas in the liquid;
   ensuring that the device is calibrated for concentrations of about 0% of the gas in the liquid and about 100% of the gas;
   using the device to conduct sufficient measurements of the gas concentration at known actual concentrations to permit generation of a first mathematical function representing device-measured concentrations versus actual concentrations of the gas in the liquid below the solubility threshold of the gas in the liquid;
   using the device-measured concentrations and the solubility threshold to fully define the first function and deducing a theoretical device-response at about the solubility threshold; and
   using the theoretical device-response at about the solubility threshold and the device calibrated response at 100% gas concentration to determine a second mathematical function representative of the device-measured concentration versus actual concentration for the region above the solubility threshold wherein the actual concentration includes an amount of gas that is solubilized in the liquid and an amount of gas that is present in bubble state; and
   using the first mathematical function and the second mathematical function to generate the correction factor.

41. The method of claim 40 wherein sufficient measurements is one measurement between 0% concentration of the gas in the liquid and the concentration of the gas in the liquid at the solubility threshold.

42. The method of claim 40 wherein sufficient measurements is at least two measurements.

43. The method of claim 40 wherein the known actual gas concentrations are less than about half of the gas concentration at the solubility threshold.

44. The method of claim 40 wherein the first mathematical function and the second mathematical function are each linear.

45. The method of claim 40 wherein the step of obtaining the solubility threshold is performed at any time prior to the step of applying the first mathematical function.

46. The method of claim 40 wherein the correction factor is the difference between a value of the first mathematical function or the second mathematical function and an actual gas concentration corresponding to that value and the difference is recorded and applied to any measured concentrations corresponding to the value.

47. The method of claim 40 wherein the correction factor is generated as the inverse function of at least one of the first mathematical function and the second mathematical function.

48. The method according to claim 40 wherein the device is a gas semipermeable membrane device.

49. A method for obtaining a correction factor for measuring a concentration of a gas in a liquid using a gas-in-liquid concentration measurement device, the method comprising:
   obtaining the solubility threshold for the gas in the liquid;
   ensuring that the device is calibrated for concentrations of about 0% of the gas in the liquid and about 100% of the gas;
   using the device to conduct sufficient measurements of the gas concentration at known actual concentrations to permit generation of a first mathematical function representing device-measured concentration versus actual concentration of the gas in the liquid below the solubility threshold of the gas in the liquid;
   determining a measured concentration at about the solubility threshold; and
   using the measured concentration at about the solubility threshold and the device calibrated response at 100% gas concentration to determine a second mathematical function representative of the device-measured concentration versus actual concentration above the solubility threshold; and
   using the first mathematical function and the second mathematical function to generate the correction factor.

50. The method of claim 49 wherein the correction factor is the difference between a value of the first mathematical function or the second mathematical function and an actual gas concentration corresponding to that value and the difference is recorded and applied to any measured concentrations corresponding to the value.

51. The method of claim 49 wherein the correction factor is generated as the inverse function of at least one of the first mathematical function and the second mathematical function.

52. The method of claim 49 wherein the measured concentration at about the solubility threshold is determined by extrapolation of the first mathematical function.

53. The method of claim 49 wherein the measured concentration at about the solubility threshold is measured using the device.

54. The method of claim 49 wherein sufficient measurements is one measurement between 0% concentration of the gas in the liquid and the concentration of the gas in the liquid at the solubility threshold.

55. The method of claim 49 wherein sufficient measurements is at least two measurements.

56. The method of claim 49 wherein the known actual gas concentrations are less than about half of the gas concentration at the solubility threshold.

57. The method of claim 49 wherein the first mathematical function and the second mathematical function are each linear.

58. The method according to claim 49 wherein the device is a gas semipermeable membrane device.

59. The method of claim 49 wherein the step of obtaining the solubility threshold is performed at any time prior to a step wherein the solubility threshold must be known.

* * * * *